US008372920B2

(12) United States Patent
Walden

(10) Patent No.: US 8,372,920 B2
(45) Date of Patent: Feb. 12, 2013

(54) WATER-ABSORBING POLYMER STRUCTURE WITH IMPROVED COLOR STABILITY

(75) Inventor: Mirko Walden, Herten (DE)

(73) Assignee: Evonik Stockhausen GmbH, Krefeld (DE)

( * ) Notice: Subject to any disclaimer, the term of this patent is extended or adjusted under 35 U.S.C. 154(b) by 362 days.

(21) Appl. No.: 12/740,054

(22) PCT Filed: Nov. 7, 2008

(86) PCT No.: PCT/EP2008/065123
§ 371 (c)(1),
(2), (4) Date: Jul. 23, 2010

(87) PCT Pub. No.: WO2009/060062
PCT Pub. Date: May 14, 2009

(65) Prior Publication Data
US 2010/0286287 A1    Nov. 11, 2010

(30) Foreign Application Priority Data
Nov. 8, 2007  (DE) .................. 10 2007 053 619

(51) Int. Cl.
*C09K 3/00* (2006.01)
*A61K 47/32* (2006.01)

(52) U.S. Cl. ............ 525/330.2; 524/437; 524/500; 524/418; 514/772.6; 252/194

(58) Field of Classification Search ............ 525/330.2; 524/437, 500, 418; 514/772.6; 252/194
See application file for complete search history.

(56) References Cited

U.S. PATENT DOCUMENTS

| | | | |
|---|---|---|---|
| 4,076,663 A | 2/1978 | Masuda et al. | |
| 4,131,576 A | 12/1978 | Iovine et al. | |
| 4,179,367 A | 12/1979 | Barthell et al. | |
| 4,286,082 A | 8/1981 | Tsubakimoto et al. | |
| 4,340,706 A | 7/1982 | Obayashi et al. | |
| 4,587,308 A | 5/1986 | Makita et al. | |
| 5,180,804 A | 1/1993 | Niessner et al. | |
| 5,409,771 A | 4/1995 | Dahmen et al. | |
| 5,610,220 A | 3/1997 | Klimmek et al. | |
| 5,672,633 A | 9/1997 | Brehm et al. | |
| 5,712,316 A | 1/1998 | Damhen et al. | |
| 6,060,557 A | 5/2000 | Dahmen et al. | |
| 6,359,049 B1 * | 3/2002 | Carrico et al. ............... | 524/414 |
| 6,403,700 B1 | 6/2002 | Dahmen et al. | |
| 7,244,812 B2 | 7/2007 | Muller et al. | |
| 7,541,395 B2 | 6/2009 | Reimann et al. | |
| 2006/0029782 A1 | 2/2006 | Harren et al. | |
| 2007/0066754 A1 | 3/2007 | Loeker et al. | |
| 2008/0214740 A1 | 9/2008 | Harren et al. | |
| 2008/0221277 A1 | 9/2008 | Walden et al. | |
| 2008/0280128 A1 | 11/2008 | Furno et al. | |
| 2009/0023848 A1 | 1/2009 | Ahmed et al. | |
| 2009/0105389 A1 | 4/2009 | Walden et al. | |
| 2009/0227741 A1 | 9/2009 | Walden et al. | |

FOREIGN PATENT DOCUMENTS

| | | |
|---|---|---|
| DE | 2706135 A1 | 8/1978 |
| DE | 2840010 A1 | 6/1979 |
| DE | 3503458 A1 | 8/1985 |
| DE | 3713601 A1 | 11/1988 |
| DE | 4020780 C1 | 8/1991 |
| DE | 4244548 A1 | 7/1994 |
| DE | 4418818 A1 | 1/1995 |
| DE | 4333056 A1 | 3/1995 |
| DE | 19529348 A1 | 2/1997 |
| DE | 10249821 A1 | 5/2004 |
| DE | 10334286 A1 | 3/2005 |
| EP | 0412363 A2 | 2/1991 |
| WO | 9605234 A1 | 2/1996 |
| WO | 9934843 A1 | 7/1999 |
| WO | 02056812 A2 | 7/2002 |
| WO | 2004022609 A1 | 3/2004 |
| WO | 2004037903 A2 | 5/2004 |
| WO | 2004084962 A1 | 10/2004 |
| WO | 2009011717 A1 | 1/2009 |

OTHER PUBLICATIONS

Iqbal Ahmed et al., Office Action dated Feb. 3, 2010 for U.S. Appl. No. 11/778,372.
International Search Report mailed on Feb. 10, 2009 in PCT/EP2008/065123.
Written Opinion (German) mailed on Feb. 10, 2009 in PCT/EP2008/065123.

* cited by examiner

*Primary Examiner* — Robert D. Harlan
(74) *Attorney, Agent, or Firm* — Smith Moore Leatherwood LLP; Philip P. McCann

(57) ABSTRACT

The present invention relates to a water-absorbing polymer structure comprising about 10 to about 100,000 ppm, based on the solids content of the water-absorbing polymer structure, of a non-polymerized sulphonate, a non-polymerized salt of a sulphonate or a mixture of a non-polymerized sulphonate and a non-polymerized salt of a sulphonate, and less than 1,000 ppm, based on the solids content of the water-absorbing polymer structure, of non-polymerized sulphites, non-polymerized bisulfites, non-polymerized sulphinates or non-polymerized salts of these compounds.

26 Claims, No Drawings

WATER-ABSORBING POLYMER STRUCTURE WITH IMPROVED COLOR STABILITY

This application is a national stage application under 35 U.S.C. §371 of international application No. PCT/EP2008/065123 filed 7 Nov. 2008, which claims priority to German Application No. DE 10 2007 053 619.6 filed 8 Nov. 2007, the disclosures of which are expressly incorporated herein by reference.

The present invention relates to a process for the production of water-absorbing polymer structures. The invention also relates to the water-absorbing polymer structures obtainable by this process, water-absorbing polymer structures, a composite, a process for the production of a composite, the composite obtainable by this process, chemical products, such as foams, shaped articles, fibers, foils, films, cables, sealing materials, liquid-absorbing hygiene articles, carriers for plant and fungal growth-regulating agents, packaging materials, soil additives or building materials, and the use of water-absorbing polymer structures.

Superabsorbers are water-insoluble, crosslinked polymers which are capable, by swelling and formation of hydrogels, of taking up large amounts of water, aqueous liquids, in particular body fluids, preferably urine or blood, and retaining these under pressure. Superabsorbers preferably absorb at least 100 times their own weight of water. Further details on superabsorbers are disclosed in "Modern Superabsorbent Polymer Technology", F. L. Buchholz, A. T. Graham, Wiley-VCH, 1998". As a result of these characteristic properties, these water-absorbing polymers are chiefly incorporated into sanitary articles, such as, for example, babies' nappies, incontinence products or sanitary towels.

The superabsorbers currently commercially available are essentially crosslinked polyacrylic acids or crosslinked starch-acrylic acid graft polymers, in which some of the carboxyl groups are neutralized with sodium hydroxide solution or potassium hydroxide solution. These are obtainable by subjecting monomeric acrylic acid or salts thereof to free radical polymerization in the presence of suitable crosslinking agents. In this context, various polymerization processes can be used, such as, for example, solution polymerization, emulsion polymerization or suspension polymerization. In the end, water-absorbing polymers in particulate form having a particle diameter in a range of from 150 to 850 µm are obtained by these various processes, and are then incorporated into the sanitary articles.

However, such superabsorbers tend to discolor during relatively long storage. In addition, there is the tendency for their clean, fresh white to discolor to honey-brown to accelerate further with increasing storage times, temperatures and atmospheric humidities. Needless to say, under temperate climate conditions such as prevail in the United States of America and in Europe, the speed of discoloration of a superabsorber is so slow that the superabsorber or the superabsorber-containing product is usually already used up before a change in color can be detected with the naked eye. In tropical and subtropical climate zones, such as in South America and South-East Asia, however, discoloration of the superabsorber proceeds so rapidly that a change in color occurs even before the superabsorber or the superabsorber-containing product is used.

The initiators, such as, for example, ascorbic acid and sodium peroxodisulfate, and inhibitors, which as a rule are contained in the acrylic acid employed, for the purpose of preventing spontaneous polymerization, such as, for example, the monomethyl ether of hydroquinone (MEHQ), employed in the free radical polymerization and remaining in the polymer are primarily responsible for the discoloration of the superabsorber.

To improve the color stability of superabsorbers, WO-A-2004/084962 therefore proposes adding to the monomer solution a sulphinate or a salt of a sulphinate instead of the conventional initiator systems comprising persulphates. Concretely, the products BRUGGOLITE®FF6 and BRUGGOLITE®FF7 commercially obtainable from Brüggemann Chemical, Heilbronn, Germany are added to the monomer solution as the initiator system in WO-A-2004/084962, the product BRUGGOLITE®FF6 being a mixture of 2-hydroxy-2-sulphinatoacetic acid disodium salt, sodium sulphite and 2-hydroxy-2-sulphonatoacetic acid disodium salt, while BRUGGOLITE®FF7 contains pure 2-hydroxy-2-sulphinatoacetic acid.

The process described in WO-A-2004/084962 for improving the color stability has the disadvantage, however, that the sulphinates employed there as the initiator system or the mixtures of sulphinates, sulphonates and sulphites employed there as the initiator system are poorer initiators of the free radical polymerization under certain conditions compared with the peroxides conventionally employed. The improved color stability is therefore also at the expense of the polymerization reaction, and consequently also at the expense of the absorption properties of the polymers obtained in this polymerization reaction.

The present invention was based on the object of overcoming the disadvantages emerging from the prior art.

In particular, the present invention was based on the object of providing a process for the production of water-absorbing polymer structures of improved color stability, the polymers obtainable by this process also being characterized by good odor stability.

The present invention was also based on the object of providing a process for the production of water-absorbing polymer structures of improved color stability in which conventional initiator systems which have proved entirely advantageous can be resorted to.

The present invention was moreover based on the object of providing water-absorbing polymer structures of improved color stability which, in spite of their improved color stability, are not inferior to the polymers known from the prior art with respect to their absorption properties.

The present invention was furthermore based on the object of providing a composite, for example a hygiene article, which likewise has an improved color stability compared with the hygiene articles known from the prior art, with at the same time a good odor stability and further good use properties.

A contribution towards achieving the abovementioned objects is made by a process for the production of water-absorbing polymer structures, comprising the process steps:
i) provision of an aqueous monomer solution containing
   a polymerizable, monoethylenically unsaturated monomer ($\alpha1$) carrying acid groups or a salt thereof or a polymerizable, monoethylenically unsaturated monomer containing a protonated or quaternized nitrogen, or a mixture of these monomers, a polymerizable, monoethylenically unsaturated monomer carrying acid groups being particularly preferred and acrylic acid being most preferred,
   optionally a monoethylenically unsaturated monomer ($\alpha2$) which can be polymerized with the monomer ($\alpha1$), and
   optionally a crosslinking agent ($\alpha3$),
ii) free radical polymerization of the aqueous monomer solution to give a polymer gel, iii) optionally comminution of the polymer gel,
iv) drying of the optionally comminuted polymer gel to give water-absorbing polymer structures,
v) optionally grinding and sieving of the water-absorbing polymer structures and
vi) surface post-crosslinking of the optionally ground and sieved water-absorbing polymer structures, wherein a reducing agent comprising a sulphonate, a salt of a sulphonate or a mixture of a sulphonate and a salt of a sulphonate is added to I) the aqueous monomer solution before or while carrying out process step ii),
II) the polymer gel after carrying out process step ii),
III) the optionally comminuted polymer gel after carrying out process step iii),
IV) the water-absorbing polymer structure after carrying out process step iv),
V) the water-absorbing polymer structure after carrying out process step v), or
VI) the water-absorbing polymer structure after carrying out process step vi), but particularly preferably to the water-absorbing polymer structure after carrying out process step iv) or after carrying out process step v), but before carrying out process step vi).

Polymer structures which are preferred according to the invention are fibers, foams or particles, fibers and particles being preferred and particles being particularly preferred.

Polymer fibers which are preferred according to the invention have dimensions such that they can be incorporated into or as yarns for textiles and also directly into textiles. It is preferable according to the invention for the polymer fibers to have a length in the range of from 1 to 500 mm, preferably 2 to 500 mm and particularly preferably 5 to 100 mm and a diameter in the range of from 1 to 200 denier, preferably 3 to 100 denier and particularly preferably 5 to 60 denier.

Polymer particles which are preferred according to the invention have dimensions such that they have an average particle size in accordance with ERT 420.2-02 in the range of from 10 to 3,000 μm, preferably 20 to 2,000 μm and particularly preferably 150 to 850 μm. In this context, it is particularly preferable for the content of polymer particles having a particle size in a range of from 300 to 600 μm to be at least 30 wt. %, particularly preferably at least 40 wt. % and most preferably at least 50 wt. %, based on the total weight of the post-crosslinked, water-absorbing polymer particles.

According to a particular embodiment of the process according to the invention, the polymer particles have dimensions such that they have an average particle size in accordance with ERT 420.2-02 in the range of from 150 to 710 μm, particularly preferably in the range of from 150 to 600 μm.

In process step i) of the process according to the invention, an aqueous monomer solution is first provided.

The monoethylenically unsaturated monomers ($\alpha 1$) carrying acid groups can be partly or completely, preferably partly neutralized. Preferably, the monoethylenically unsaturated monomers carrying acid groups are neutralized to the extent of at least 25 mol %, particularly preferably to the extent of at least 50 mol % and moreover preferably to the extent of 50-80 mol %. Reference is made in this connection to DE 195 29 348 A1, the disclosure of which is introduced herewith as reference. The neutralization can also take place partly or completely after the polymerization. Furthermore, the neutralization can be carried out with alkali metal hydroxides, alkaline earth metal hydroxides, ammonia and carbonates and bicarbonates. In addition, any further base which forms a water-soluble salt with the acid is conceivable. Mixed neutralization with various bases is also conceivable. Neutralization with ammonia and alkali metal hydroxides is preferred, particularly preferably with sodium hydroxide and with ammonia.

Furthermore, the free acid groups can predominate in a water-absorbing polymer structure obtainable by the process according to the invention, so that this polymer structure has a pH in the acid range. This acid water-absorbing polymer structure can be at least partly neutralized by a polymer structure having free basic groups, preferably amine groups, which is basic in comparison with the acid polymer structure. These polymer structures are called "mixed-bed ion exchange absorbent polymers" (MBIEA polymers) in the literature and are disclosed, inter alia, in WO 99/34843 A1. The disclosure of WO 99/34843 A1 is introduced herewith as reference and therefore forms part of the disclosure. As a rule, MBIEA polymers are a composition which comprises on the one hand basic polymer structures which are capable of exchanging anions, and on the other hand a polymer structure which is acid in comparison with the basic polymer structure and is capable of exchanging cations. The basic polymer structure contains basic groups and is typically obtained by polymerization of monomers ($\alpha 1$) which carry basic groups or groups which can be converted into basic groups. These monomers are above all those which contain primary, secondary or tertiary amines or the corresponding phosphines or at least two of the above functional groups. This group of monomers includes, in particular, ethyleneamine, allylamine, diallylamine, 4-aminobutene, alkyloxycyclins, vinylformamide, 5-aminopentene, carbodiimide, formaldacin, melamine and the like, and secondary or tertiary amine derivatives thereof.

Preferred monoethylenically unsaturated monomers ($\alpha 1$) carrying acid groups are preferably those compounds which are mentioned as ethylenically unsaturated monomers ($\alpha 1$) containing acid groups in WO 2004/037903 A2, which is introduced herewith as reference and thus forms part of the disclosure. Particularly preferred monoethylenically unsaturated monomers ($\alpha 1$) carrying acid groups are acrylic acid and methacrylic acid, acrylic acid being most preferred.

Acrylamides, methacrylamides or vinylamides can be employed as monoethylenically unsaturated monomers ($\alpha 2$) which can be copolymerized with the monomers ($\alpha 1$).

Preferred (meth)acrylamides are, in addition to acrylamide and methacrylamide, alkyl-substituted (meth)acrylamides or aminoalkyl-substituted derivatives of (meth)acrylamide, such as N-methylol(meth)acrylamide, N,N-dimethylamino (meth)acrylamide, dimethyl-(meth)acrylamide or diethyl (meth)acrylamide. Possible vinylamides are, for example, N-vinylamides, N-vinylformamides, N-vinylacetamides, N-vinyl-N-methylacetamides, N-vinyl-N-methylformamides and vinylpyrrolidone. Among these monomers, acrylamide is particularly preferred.

Water-soluble monomers can furthermore be employed as monoethylenically unsaturated monomers ($\alpha 2$) which can be copolymerized with the monomers ($\alpha 1$). In this connection, alkoxypolyalkylene oxide(meth)acrylates, such as methoxypolyethylene glycol (meth)acrylates, are preferred in particular.

Water-dispersible monomers are furthermore conceivable as monoethylenically unsaturated monomers ($\alpha 2$) which can be copolymerized with the monomers ($\alpha 1$). Preferred water-dispersible monomers are acrylic acid esters and methacrylic acid esters, such as methyl(meth)acrylate, ethyl(meth)acrylate, propyl(meth)acrylate or butyl(meth)acrylate.

The monoethylenically unsaturated monomers (α2) which can be copolymerized with (α1) can also include methylpolyethylene glycol allyl ether, vinyl acetate, styrene and isobutylene.

Those compounds which are mentioned as crosslinking agents (α3) in WO 2004/037903 A2 are preferably employed as crosslinking agents (α3). Among these crosslinking agents, water-soluble crosslinking agents are particularly preferred. In this context, N,N'-methylenebisacrylamide, polyethylene glycol di(meth)acrylates, triallylmethylammonium chloride, tetraallylammonium chloride and allylnonaethylene glycol acrylate prepared with 9 mol of ethylene oxide per mol of acrylic acid are most preferred.

In addition to the monomers (α1) and optionally (α2) and optionally the crosslinking agent (α3), the monomer solution can also comprise water-soluble polymers (α4). Preferred water-soluble polymers (α4) include partly or completely saponified polyvinyl alcohol, polyvinylpyrrolidone, starch or starch derivatives, polyglycols or polyacrylic acid. The molecular weight of these polymers is not critical, as long as they are water-soluble. Preferred water-soluble polymers (α4) are starch or starch derivatives or polyvinyl alcohol. The water-soluble polymers (α4), preferably synthetic, such as polyvinyl alcohol, can not only serve as a graft base for the monomers to be polymerized. It is also conceivable for these water-soluble polymers to be mixed with the polymer gel or the already dried, water-absorbing polymer gel only after the polymerization.

The monomer solution can furthermore also comprise auxiliary substances (α5), these auxiliary substances including, in particular, the initiators which may be necessary for the polymerization, complexing agents, such as, for example, EDTA, and in particular also thermoplastic polymers or dispersions containing thermoplastic polymers.

Possible solvents for the monomer solution are water, organic solvents or mixtures of water and organic solvents, the choice of the solvent also depending in particular on the nature and method of the polymerization.

The relative amount of monomers (α1) and (α2) and of crosslinking agents (α3) and water-soluble polymers (α4) and auxiliary substances (α5) in the monomer solution is preferably chosen such that the water-absorbing polymer structure obtained in process step iv) after drying is based

- to the extent of 20-99.999 wt. %, preferably to the extent of 55-98.99 wt. % and particularly preferably to the extent of 70-98.79 wt. % on the monomers (α1),
- to the extent of 0-80 wt. %, preferably to the extent of 0-44.99 wt. % and particularly preferably to the extent of 0.1-44.89 wt. % on the monomers (α2),
- to the extent of 0-5 wt. %, preferably to the extent of 0.001-3 wt. % and particularly preferably to the extent of 0.01-2.5 wt. % on the crosslinking agents (α3),
- to the extent of 0-30 wt. %, preferably to the extent of 0-5 wt. % and particularly preferably to the extent of 0.1-5 wt. % on the water-soluble polymers (α4),
- to the extent of 0-20 wt. %, preferably to the extent of 0-10 wt. % and particularly preferably to the extent of 0.1-8 wt. % on the auxiliary substances (α5), and
- to the extent of 0.5-25 wt. %, preferably to the extent of 1-10 wt. % and particularly preferably to the extent of 3-7 wt. % on water (α6), the sum of the amounts by weight (α1) to (α6) being 100 wt. %.

Optimum values for the concentration in particular of the monomers, crosslinking agents and water-soluble polymers in the monomer solution can be determined by simple preliminary experiments or from the prior art, in particular the publications U.S. Pat. No. 4,286,082, DE 27 06 135 A1, U.S. Pat. No. 4,076,663, DE 35 03 458 A1, DE 40 20 780 C1, DE 42 44 548 A1, DE 43 33 056 A1 and DE 44 18 818 A1.

In process step ii) of the process according to the invention, the aqueous monomer solution obtained in process step i) is subjected to free radical polymerization to give a polymer gel, in principle all the polymerization processes known to the person skilled in the art being possible. For example, bulk polymerization, which is preferably carried out in kneading reactors, such as extruders, solution polymerization, spray polymerization, inverse emulsion polymerization and inverse suspension polymerization are to be mentioned in this connection.

The solution polymerization is preferably carried out in water as the solvent. The solution polymerization can be carried out continuously or discontinuously. A broad spectrum of possibilities of variation in respect of the reaction circumstances, such as temperatures, nature and amount of the initiators and also of the reaction solution, is to be found from the prior art. Typical processes are described in the following patent specifications: U.S. Pat. No. 4,286,082, DE 27 06 135 A1, U.S. Pat. No. 4,076,663, DE 35 03 458 A1, DE 40 20 780 C1, DE 42 44 548 A1, DE 43 33 056 A1 and DE 44 18 818 A1. The disclosures are introduced herewith as reference and therefore form part of the disclosure.

The polymerization is initiated by an initiator as is generally conventional. Initiators which can be used for initiation of the polymerization are all the initiators which form free radicals under the polymerization conditions and are conventionally employed in the preparation of superabsorbers. Initiation of the polymerization by the action of electron beams on the polymerizable aqueous mixture is also possible. Nevertheless, the polymerization can also be initiated in the absence of initiators of the abovementioned type by the action of high-energy radiation in the presence of photoinitiators. Polymerization initiators can be contained in dissolved or dispersed form in a solution of monomers according to the invention. Possible initiators are all the compounds known to the person skilled in the art which dissociate into free radicals. These include, in particular, those initiators which have already been mentioned as possible initiators in WO 2004/037903 A2.

A redox system comprising hydrogen peroxide, sodium peroxodisulphate and ascorbic acid is particularly preferably employed for preparation of the water-absorbing polymer structures. In this connection it is particularly preferable for more than 300 ppm of a persulphate, in particular more than 300 ppm of sodium peroxodisulphate, based on the total weight of the monomer solution, to be added to the monomer solution.

Inverse suspension and emulsion polymerization can also be used in the process according to the invention. According to these processes, an aqueous, partly neutralized solution of monomers (α1) and (α2), optionally containing water-soluble polymers (α4) and auxiliary substances (α5), is dispersed in a hydrophobic organic solvent with the aid of protective colloids and/or emulsifiers and the polymerization is started by free radical initiators. The crosslinking agents (α3) either are dissolved in the monomer solution and are metered together with this, or are added separately and optionally during the polymerization. The addition of a water-soluble polymer (α4) as a graft base is optionally carried out via the monomer solution or by direct initial introduction into the oily phase. The water is then removed azeotropically from the mixture and the polymer is filtered off.

Both in the case of solution polymerization and in the case of inverse suspension and emulsion polymerization, the crosslinking can furthermore be carried out by polymerizing in the polyfunctional crosslinking agent (α3) dissolved in the monomer solution and/or by reaction of suitable crosslinking agents with functional groups of the polymer during the polymerization steps. The processes are described, for example, in the publications U.S. Pat. No. 4,340,706, DE 37 13 601 A1, DE 28 40 010 A1 and WO 96/05234 A1, the corresponding disclosure of which is introduced herewith as reference.

In process step iii) of the process according to the invention, the polymer gel obtained in process step ii) is optionally comminuted, this comminution being carried out in particular if the polymerization is carried out by means of a solution polymerization. The comminution can be carried out by comminution devices known to the person skilled in the art, such as, for example, a mincing machine.

In process step iv) of the process according to the invention, the optionally previously comminuted polymer gel is dried. Drying of the polymer gel is preferably carried out in suitable dryers or ovens. Rotary tube ovens, fluidized bed dryers, plate dryers, paddle dryers or infrared dryers may be mentioned by way of example. It is furthermore preferable according to the invention for the drying of the polymer gel in process step iv) to be carried out down to a water content of from 0.5 to 25 wt. %, preferably from 1 to 10 wt. %, the drying temperatures conventionally being in a range of from 100 to 200 ° C.

In process step v) of the process according to the invention, the water-absorbing polymer structures obtained in process step iv) can be ground again, especially if they have been obtained by solution polymerization, and sieved to the abovementioned desired grain size. The grinding of the dried, water-absorbing polymer structures is preferably carried out in suitable mechanical comminution devices, such as, for example, a ball mill, while the sieving can be carried out, for example, using sieves of suitable mesh width.

In process step vi) of the process according to the invention, the optionally ground and sieved water-absorbing polymer structures are post-crosslinked on the surface. For the surface post-crosslinking, the dried and optionally ground and sieved water-absorbing polymer structures from process step iv) or v), but the not yet dried but preferably already comminuted polymer gel from process step ii) or iii), is brought into contact with a preferably organic, chemical surface post-crosslinking agent. In this context, the post-crosslinking agent, especially if it is not liquid under the post-crosslinking conditions, is preferably brought into contact with the water-absorbing polymer structure or the polymer gel in the form of a fluid $F_1$ containing the post-crosslinking agent and a solvent. In this context, solvents which are employed are, preferably, water, water-miscible organic solvents, such as, for example, methanol, ethanol, 1-propanol, 2-propanol or 1-butanol, or mixtures of at least two of these solvents, water being most preferred as the solvent. It is furthermore preferable for the fluid $F_1$ to contain the post-crosslinking agent in an amount in a range of from 5 to 75 wt. %, particularly preferably 10 to 50 wt. % and most preferably 15 to 40 wt. %, based on the total weight of the fluid $F_1$.

In the process according to the invention, the water-absorbing polymer structure or the optionally comminuted polymer gel is preferably brought into contact with the fluid $F_1$ containing the post-crosslinking agent by thorough mixing of the fluid $F_1$ with the polymer structure or the polymer gel.

Suitable mixing units for the application of the fluid $F_1$ are e.g. the Patterson-Kelley mixer, DRAIS turbulence mixer, Lodige mixer, Ruberg mixer, screw mixers, plate mixers and fluidized bed mixers and continuously operating vertical mixers, in which the polymer structure is mixed by means of rotating blades in rapid frequency (Schugi mixer).

In the process according to the invention, during the post-crosslinking the polymer structure or the polymer gel is preferably brought into contact with at most 20 wt. %, particularly preferably with at most 15 wt. %, moreover preferably with at most 10 wt. %, moreover even more preferably with at most 5 wt. % of solvent, preferably water.

In the case of polymer structures in the form of preferably spherical particles, it is furthermore preferable according to the invention for the bringing into contact to be effected merely by bringing the outer region, but not the inner region of the particulate polymer structures into contact with the post-crosslinking agent or with the fluid $F_1$.

Compounds which have at least two functional groups which can react with functional groups of a polymer structure in a condensation reaction (=condensation crosslinking agents), in an addition reaction or in a ring-opening reaction are preferably understood as post-crosslinking agents which are employed in the process according to the invention. Those post-crosslinking agents that have been mentioned as crosslinking agents of crosslinking agent class II in WO 2004/037903 A2 are preferred as post-crosslinking agents in the process according to the invention.

Among these compounds, particularly preferred post-crosslinking agents are condensation crosslinking agents, such as, for example, diethylene glycol, triethylene glycol, polyethylene glycol, glycerol, polyglycerol, propylene glycol, diethanolamine, triethanolamine, polyoxypropylene, oxyethylene/oxypropylene block copolymers, sorbitan fatty acid esters, polyoxyethylene sorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one and 1,3-dioxolan-2-one.

After the polymer structures or the polymer gels have been brought into contact with the post-crosslinking agent or with the fluid $F_1$ containing the post-crosslinking agent, they are heated to a temperature in the range of from 50 to 300° C., preferably 75 to 275° C. and particularly preferably 150 to 250° C., so that preferably as a result the outer region of the polymer structures is more highly crosslinked compared with the inner region (=post-crosslinking), and if polymer gel is employed, this is also dried at the same time. The duration of the heat treatment is limited by the risk that the desired profile of properties of the polymer structures is destroyed as a result of the action of heat.

According to the process according to the invention, a reducing agent comprising a sulphonate, a salt of a sulphonate or a mixture of a sulphonate and a salt of a sulphonate is added to I) the aqueous monomer solution before or while carrying out process step ii),
II) the polymer gel after carrying out process step ii),
III) the optionally comminuted polymer gel after carrying out process step iii),
IV) the water-absorbing polymer structure after carrying out process step iv),
V) the water-absorbing polymer structure after carrying out process step v), or
VI) the water-absorbing polymer structure after carrying out process step vi).

Each of the abovementioned alternatives I), II), III), IV) and VI) represents a preferred embodiment of the process according to the invention, it also being possible for the reducing agent to be added at several different points in time.

For example, addition of the reducing agent to the monomer solution according to alternative I) and addition of the reducing agent to the dried, ground and sieved water-absorbing polymer structure according to alternative V) is conceivable.

According to a first and particularly preferred variant of the process according to the invention, however, the reducing agent is added after carrying out process step iv) or after carrying out process step v), but before carrying out process step vi), it possibly proving to be advantageous in particular to add the reducing agent to the fluid $F_1$ comprising the post-crosslinking agent and the solvent. However, it is also conceivable to add the reducing agent in the form of a separate fluid $F_2$ comprising the reducing agent and a solvent, for example water, water-miscible organic solvents, such as, for example, methanol, ethanol, 1-propanol, 2-propanol or 1-butanol, or mixtures of at least two of these solvents, water in particular being the solvent in the fluid $F_2$, before or during or after application of the fluid $F_1$. After the two components (reducing agent and post-crosslinking agent) have been brought into contact with the water-absorbing polymer structure in this manner, post-crosslinking according to process step vi) of the process according to the invention is carried out by heating the mixture obtained in this way up to the temperature ranges mentioned above in connection with the surface post-crosslinking.

According to a second particularly preferred variant of the process according to the invention, the reducing agent is brought into contact with the water-absorbing polymer structure after carrying out process step vi). For this, the reducing agent can be mixed, for example, in the form of the fluid $F_2$ described above with the water-absorbing polymer structure which has already been post-crosslinked on the surface.

In connection with the reducing agent employed, it is furthermore preferable for this to comprise less than 10 wt. %, particularly preferably less than 5 wt. %, even more preferably less than 1 wt. %, in each case based on the total weight of the reducing agent, of sulfur compounds which differ from sulphonates and sulphonate salts, in particular less than 10 wt. %, particularly preferably less than 5 wt. %, even more preferably less than 1 wt. % of sulphites, bisulfites, sulphinates, in particular 2-hydroxy-2-sulphinatoacetic acid, or salts, in particular sodium salts, of these sulfur compounds, most preferably sodium sulphite and the disodium salt of 2-hydroxy-2-sulphinatoacetic acid. In particular less than 1,000 ppm, particularly preferably less than 500 ppm and even more preferably less than 100 ppm, in each case based on the solids content of the water-absorbing polymer structure, but most preferably no amount at all of sulfur compounds which differ from sulphonates and sulphonate salts are employed in the process according to the invention for treatment of the polymer gel obtained after carrying out process step ii), the comminuted polymer gel obtained after carrying out process step iii), the water-absorbing polymer structure obtained after carrying out process step iv), the water-absorbing polymer structure obtained after carrying out process step v) or the water-absorbing polymer structure obtained after carrying out process step vi). Preferably, the reducing agent employed consists to the extent of at least 90 wt. %, particularly preferably to the extent of at least 95 wt. % and most preferably to the extent of at least 99 wt. %, in each case based on the total weight of the reducing agent employed, of sulphonates, of salts of sulphonates or of a mixture of sulphonates and salts of sulphonates.

The wording "comprising less than 10 wt. %, particularly preferably less than 5 wt. %, even more preferably less than 1 wt. % of sulphites, bisulfites, sulphinates or salts of these sulfur compounds" is to be understood in this context as meaning that the total amount of sulphites, bisulfites, sulphinates or salts of these sulfur compounds is less than 10 wt. %, particularly preferably less than 5 wt. %, even more preferably less than 1 wt. %.

It is furthermore preferable according to the invention for the sulphonate or the sulphonate salt contained in the reducing agent to have the structure I

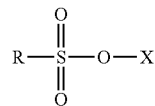

Structure 1 in which X is a hydrogen atom, an ammonium cation or an alkali metal cation and R is a saturated or unsaturated, aliphatic or aromatic $C_1$-$C_{20}$-hydrocarbon radical, particularly preferably a saturated or unsaturated, aliphatic or aromatic $C_2$-$C_{15}$-hydrocarbon radical and most preferably a saturated or unsaturated, aliphatic or aromatic $C_3$-$C_{10}$-hydrocarbon radical, a radical of the structure YOOC—$R^1$—, in which Y is a hydrogen atom, an ammonium cation or a monovalent metal cation, preferably an alkali metal cation, and $R^1$ is a $C_1$-$C_7$-alkylene radical, preferably a $C_1$-$C_5$-alkylene radical and most preferably a $C_1$-$C_3$-alkylene radical, wherein the YOOC function can optionally also be alkoxylated with 2 to 50 alkylene oxide units, particularly preferably with 4 to 20 alkylene oxide units, particularly preferably ethylene oxide or propylene oxide units, a radical of the structure ZOOC—$R^2$—, in which Z is a hydrogen atom, an ammonium cation or a monovalent metal cation, preferably an alkali metal cation, and $R^2$ is a $C_1$-$C_7$-alkylene radical, preferably a $C_1$-$C_5$-alkylene radical and most preferably a $C_1$-$C_3$-alkylene radical, which carries a hydroxyl group on at least one of the carbon atoms, wherein the ZOOC function can optionally also be alkoxylated with 2 to 50 alkylene oxide units, particularly preferably with 4 to 20 alkylene oxide units, particularly preferably ethylene oxide or propylene oxide units, a radical of the structure R'R"N—$R^3$—, in which $R^3$ is a $C_1$-$C_9$-alkylene radical, preferably a $C_2$-$C_8$-alkylene radical and most preferably a $C_3$-$C_7$-alkylene radical, and the radicals R' and R" can be a hydrogen atom, a $C_1$-$C_5$-alkyl radical or a radical of the structure R'''—CO—, in which R''' is a saturated or unsaturated $C_1$-$C_5$-hydrocarbon, or a radical of the structure $R^4$—[OCH$_2$CH$_2$]$_n$—O—$R^5$- or a radical of the structure $R^4$—[OCH$_2$CHCH$_3$]$_n$—O —$R^5$, in which $R^4$ is a $C_1$-$C_{10}$-alkyl radical or a $C_1$-$C_9$-acyl radical, n is an integer in a range of from 2 to 50, particularly preferably in a range of from 4 to 20, and $R^5$ is a $C_1$-$C_9$-alkylene radical.

Examples of sulphonates which are particularly suitable according to the invention include, in particular, vinylsulphonic acid, allylsulphonic acid, vinyltoluenesulphonnic acid, styrenesulphonic acid, sulphoethyl acrylate, sulphoethyl methacrylates, sulphopropyl acrylates, sulphopropyl methacrylates, 2-vinyl-4-ethylbenzenesulphonic acid, 2-allylbenzenesulphonic acid, 1-phenylethylenesulphonic acid, 2-hydroxy-3-methacryloxypropylsulphonic acid, 2-acrylamide-2-methylpropanesulphonic acid, para-toluenesulphonic acid, 2-hydroxy-2-sulphonatoacetic acid, the corresponding salts of the abovementioned compounds and mixtures of at least two of the abovementioned compounds.

The use of 2-hydroxy-2-sulphonatoacetic acid, in particular of the disodium salt of 2-hydroxy-2-sulphonatoacetic acid, and the use of a reducing agent which consists to the extent of at least 90 wt. %, even more preferably to the extent of at least 95 wt. % and most preferably to the extent of at least 99 wt. % of 2-hydroxy-2-sulphonatoacetic, the disodium salt of 2-hydroxy-2-sulphonatoacetic acid or mixtures of 2-hydroxy-2-sulphonatoacetic acid and the disodium salt of 2-hydroxy-2-sulphonatoacetic acid is particularly preferred according to the invention.

It is furthermore preferable according to the invention for the reducing agent to be employed in an amount in a range of from 0.001 to 10 wt. %, particularly preferably in a range of from 0.005 to 5 wt. % and most preferably in an amount in a range of from 0.01 to 1 wt. %, in each case based on the solids content of the water-absorbing polymer structure.

In addition to the surface modification of the water-absorbing polymer structures by means of surface post-crosslinking carried out in process step vi), the water-absorbing polymer structures can also be subjected to further surface modifications, which can in principle be carried out before, during or after the surface modification.

The preferred modification measure to be mentioned here is the bringing into contact of the outer region of the polymer structures with a compound containing a metal ion which is divalent or more than divalent, particularly preferably an $Al^{3+}$ ion, before, during or after the post-crosslinking (that is to say before, during or after process step vi)). In this context it is preferable for the compound containing a metal ion which is divalent or more than divalent to be brought into contact with the water-absorbing polymer structures in an amount in a range of from 0.01 to 30 wt. %, particularly preferably in an amount in a range of from 0.1 to 20 wt. % and moreover preferably in an amount in a range of from 0.3 to 5 wt. %, in each case based on the weight of the water-absorbing polymer structures.

The outer region of the water-absorbing polymer structures is preferably brought into contact with the compound containing a metal ion which is divalent or more than divalent by mixing the water-absorbing polymer structure with the compound under dry conditions, or by bringing the water-absorbing polymer structures into contact with a fluid $F_3$ comprising a solvent, preferably water, water-miscible organic solvents, such as, for example, methanol or ethanol, or mixtures of at least two of these, and the compound containing a metal ion which is divalent or more than divalent, the components being brought into contact preferably by spraying the water-absorbing polymer particles with the fluid $F_3$ and mixing.

Salts, particularly preferably water-soluble salts of metals which are divalent or more than divalent, in particular a salt of alkaline earth metal ions, such as, for example, calcium or magnesium salt, salts of aluminum, of chromium, of copper, of iron or of zinc or mixed salts of these cations, are possible in particular as the compound containing a metal ion which is divalent or more than divalent, salts of aluminum being particularly preferred.

Preferably, in this context, the compound containing a metal ion which is divalent or more than divalent is contained in the fluid $F_3$ in an amount, without taking into consideration water of crystallization, in a range of from 0.1 to 50 wt. %, particularly preferably in an amount in a range of from 1 to 30 wt. %, in each case based on the total weight of the fluid $F_3$. It is furthermore preferable for the fluid $F_3$ to be brought into contact with the polymer structures in an amount in a range of from 0.01 to 15 wt. %, particularly preferably in an amount in a range of from 0.05 to 6 wt. %, in each case based on the weight of the polymer structures.

Compounds containing $Al^{3+}$ ions are a particularly preferred compound containing a metal ion which is divalent or more than divalent, among these in turn $AlCl_3 33\ 6\ H_2O$, $NaAl(SO_4)_2 \times 12\ H_2O$, $KAl(SO_4)_2 \times 12\ H_2O$, $Al_2(SO_4)_3 \times 14\text{-}18\ H_2O$ or aluminum lactate, aluminum lactate and aluminum sulphate and hydrates of aluminum sulphate being particularly preferred. Mixtures of these aluminum compounds, in particular mixtures of aluminum lactate and aluminum sulphate, can also be employed. Compounds containing a metal ion which is divalent or more than divalent which are furthermore preferred are, in particular, mixtures of a salt containing an alkali metal cation, particularly preferably $Na^+$, and a deprotonated organic acid, particularly preferably the lactate anion, and the compound described above containing a metal ion which is divalent or more than divalent, mixtures of sodium lactate and aluminum sulphate and mixtures of sodium lactate and aluminum lactate being particularly preferred.

According to a particular embodiment of the process according to the invention, the surface modification of the water-absorbing polymer structures is carried out with the compound containing a metal ion which is divalent or more than divalent before carrying out process step vi) by bringing the water-absorbing polymer structures obtained after carrying out process step iv) or after carrying out process step v) into contact with a fluid comprising the post-crosslinking agent, the reducing agent and the compound containing a metal ion which is divalent or more than divalent, and heating the mixture to the temperatures mentioned in connection with the surface post-crosslinking.

A further surface modification measure which may be mentioned at this point, in addition to the surface post-crosslinking and the treatment with a compound containing a metal ion which is divalent or more than divalent, is also that of bringing the water-absorbing polymer structures into contact with inorganic particles, for example with finely divided silicon dioxide, which is preferably applied in aqueous suspension, or with silica sol. Coating of the water-absorbing polymer structures with so-called "anti-caking" agents, with flow auxiliaries, such as, for example, polyethylene glycols, with thermoplastic polymers, such as is described, for example, in DE-A-103 34 286, or with odor-binding agents, such as, for example, cyclodextrins or zeolites, is furthermore conceivable.

A contribution towards achieving the abovementioned objects is also made by a water-absorbing polymer structure which is obtainable by the process according to the invention described above. In this context, it is particularly preferable for the water-absorbing polymer structure according to the invention to comprise monomers carrying carboxylate groups to the extent of at least 50 wt. %, preferably to the extent of at least 70 wt. % and moreover preferably to the extent of at least 90 wt. %, in each case based on the weight of the water-absorbing polymer structures. It is further preferable according to the invention for the water-absorbing polymer structure according to the invention to be based to the extent of at least 50 wt. %, preferably to the extent of at least 70 wt. %, in each case based on the weight of the water-absorbing polymer structures, on polymerized acrylic acid, which is preferably neutralized to the extent of at least 20 mol %, particularly preferably the to extent of at least 50 mol % and moreover preferably in a range of from 60 to 85 mol %.

A contribution towards achieving the abovementioned objects is furthermore made by a water-absorbing polymer structure comprising 10 to 100,000 ppm, particularly preferably 50 to 50,000 ppm and most preferably 100 to 10,000 ppm, in each case based on the solids content of the water-absorbing polymer structure, of a non-polymerized sulphonate, a non-polymerized salt of a sulphonate or a mixture of a non-polymerized sulphonate and a non-polymerized salt of a sulphonate, and less than 1,000 ppm, particularly preferably less than 500 ppm, even more preferably less than 100 ppm, in each case based on the solids content of the water-absorbing polymer structure, of non-polymerized sulphites, non-polymerized bisulfites, non-polymerized sulphinates or non-polymerized salts of these compounds. The water-absorbing polymer structure most preferably contains no detectable amounts of non-polymerized bisulphites, non-polymerized sulphinates or non-polymerized salts of these compounds, here also the wording "comprising less than 1,000 ppm of non-polymerized sulphites, non-polymerized bisulphites, non-polymerized sulphinates or non-polymerized salts of these compounds" being understood as meaning that the total amount of sulphites, bisulphites, sulphinates or salts of the sulfur compounds is less than 1,000 ppm, particularly preferably less than 500 ppm, even more preferably less than 100 ppm.

A further contribution towards achieving the abovementioned objects is made in particular by a water-absorbing polymer structure, the surface of which has been brought into contact with 0.001 to 10 wt. %, particularly preferably with 0.001 to 5 wt. % and most preferably with 0.01 to 1 wt. %, in each case based on the solids content of the water-absorbing polymer structure, of a reducing agent comprising a sulphonate, a salt of a sulphonate or a mixture of a sulphonate and a salt of a sulphonate.

In this connection it is particularly preferable for the reducing agent to comprise less than 10 wt. %, particularly preferably less than 5 wt. %, even more preferably less than 1 wt. %, in each case based on the total weight of the reducing agent, of sulfur compounds which differ from sulphonates and sulphonate salts, in particular less than 10 wt. %, particularly preferably less than 5 wt. %, even more preferably less than 1 wt. % of sulphites, bisulphites, sulphinates or salts of these sulfur compounds.

Preferred sulphonates or salts of sulphonates in connection with the water-absorbing polymer structures according to the invention are those compounds which have already been mentioned above as preferred sulphonates and sulphonate salts in connection with the process according to the invention, the disodium salt of 2-hydroxy-2-sulphonatoacetic acid being most preferred.

According to a preferred embodiment of the water-absorbing polymer structures according to the invention or of the water-absorbing polymer structures obtainable by the process according to the invention, these have at least one of the following properties:

($\beta$1) a whiteness index, determined in accordance with the test method described herein, of at least 7.5, particularly preferably of at least 8.0, even more preferably of at least 8.5 and most preferably of at least 9.0 after storage of the water-absorbing polymer structure for 20 days at 60° C. and at 75% relative atmospheric humidity;

($\beta$2) an absorption, determined in accordance with ERT 442.2-02, under a pressure of about 50 g/cm² (0.7 psi) of at least 18 g/g, particularly preferably of at least 20 g/g and most preferably of at least 22 g/g;

($\beta$3) an SFC value (SFC="saline flow conductivity"), determined in accordance with the test method described herein, at a TB value of <26 g/g, determined in accordance with the test method described herein, of at least $80\times10^{-7}$ cm³·s·g⁻¹, preferably of at least $100\times10^{-7}$ cm³·s·g⁻¹ and particularly preferably of at least $120\times10^{-7}$ cm³·s·g⁻¹, ($\beta$4) an SFC value, determined in accordance with the test method described herein, at a TB value in the range of ≧26 to <27 g/g, determined in accordance with the test method described herein, of at least $70\times10^{-7}$ cm³·s·g⁻¹, preferably of at least $90\times10^{-7}$ cm³·s·g⁻¹ and particularly preferably of at least $110\times10^{-7}$ cm³·s·g⁻¹, ($\beta$5) an SFC value, determined in accordance with the test method described herein, at a TB value in the range of ≧27 to <28 g/g, determined in accordance with the test method described herein, of at least $60\times10^{-7}$ cm³·s·g⁻¹, preferably of at least $80\times10^{-7}$ cm³·s·g⁻¹ and particularly preferably of at least $100\times10^{-7}$ cm³·s·g⁻¹, ($\beta$6) an SFC value, determined in accordance with the test method described herein, at a TB value in the range of ≧28 to <29 g/g, determined in accordance with the test method described herein, of at least $45\times10^{-7}$ cm³·s·g⁻¹, preferably of at least $65\times10^{-7}$ cm³·s·g⁻¹ and particularly preferably of at least $85\times10^{-7}$ cm³·s·g⁻¹, ($\beta$7) an SFC value, determined in accordance with the test method described herein, at a TB value in the range of ≧29 to <30 g/g, determined in accordance with the test method described herein, of at least $30\times10^{-7}$ cm³·s·g⁻¹, preferably of at least $50\times10^{-7}$ cm³·s·g⁻¹ and particularly preferably of at least $70\times10^{-7}$ cm³·s·g⁻¹, ($\beta$8) an SFC value, determined in accordance with the test method described herein, at a TB value in the range of ≧30 to <31 g/g, determined in accordance with the test method described herein, of at least $20\times10^{-7}$ cm³·s·g⁻¹, preferably of at least $40\times10^{-7}$ cm³·s·g⁻¹ and particularly preferably of at least $60\times10^{-7}$ cm³·s·g⁻¹, ($\beta$9) an SFC value, determined in accordance with the test method described herein, at a TB value in the range of >31 g/g, determined in accordance with the test method described herein, of at least $10\times10^{-7}$ cm³·s·g⁻¹, preferably of at least $20\times10^{-7}$ cm³·s·g⁻¹ and particularly preferably of at least $30\times10^{-7}$ cm³·s·g⁻¹.

Embodiments of the water-absorbing polymer structures obtainable by the process according to the invention which are furthermore preferred have any conceivable combination of the above features ($\beta$1) to ($\beta$9), the embodiments of the following feature combinations being preferred: ($\beta$1), ($\beta$1)($\beta$2), ($\beta$1)($\beta$3), ($\beta$1)($\beta$4), ($\beta$1)($\beta$5), ($\beta$1)($\beta$6), ($\beta$1)($\beta$7), ($\beta$1)($\beta$8), ($\beta$1)($\beta$9) and ($\beta$1)($\beta$2)($\beta$3)($\beta$4)($\beta$5)($\beta$6)($\beta$7)($\beta$8)($\beta$9)

In this context it is preferable for the water-absorbing polymer structure according to the invention to have the same properties as the water-absorbing polymer structure obtainable by the process according to the invention. It is also preferable according to the invention for those values which have been stated in connection with the process according to the invention and the water-absorbing polymer structures according to the invention as lower limits of features according to the invention without upper limits to be 20 times, preferably 10 times and particularly preferably 5 times the most preferred value of the lower limit.

A further contribution towards achieving the objects described above is made by a composite comprising the water-absorbing polymer structures according to the invention or the water-absorbing polymer structures obtainable by the process according to the invention and a substrate. In this context it is preferable for the polymer structures according to the invention and the substrate to be firmly bonded to one another. Preferred substrates are films of polymers, such as, for example, of polyethylene, polypropylene or polyamide, metals, nonwovens, fluff, tissues, woven fabric, natural or synthetic fibers, or other foams. It is furthermore preferable according to the invention for the composite to include at least one region which comprises the water-absorbing polymer structure according to the invention in an amount in the range of from about 15 to 100 wt. %, preferably about 30 to 100 wt. %, particularly preferably from about 50 to 99.99 wt. %, furthermore preferably from about 60 to 99.99 wt. % and moreover preferably from about 70 to 99 wt. %, in each case based on the total weight of the composite region in question, this region preferably having a size of at least 0.01 cm$^3$, preferably at least 0.1 cm$^3$ and most preferably at least 0.5 cm$^3$.

In a particularly preferred embodiment of the composite according to the invention, this is a planar composite such as is described as "absorbent material" in WO 02/056812 A1. The disclosure content of WO 02/056812 A1, in particular with respect to the precise structure of the composite, the weight per unit area of its constituents and its thickness, is introduced herewith as reference and represents a part of the disclosure of the present invention.

A further contribution towards achieving the abovementioned objects is made by a process for the production of a composite, wherein the water-absorbing polymer structures according to the invention or the water-absorbing polymer structures obtainable by the process according to the invention and a substrate and optionally an additive are brought into contact with one another. Substrates which are employed are preferably those substrates which have already been mentioned above in connection with the composite according to the invention.

A contribution towards achieving the abovementioned objects is also made by a composite obtainable by the process described above, this composite preferably having the same properties as the composite according to the invention described above.

A further contribution towards achieving the abovementioned objects is made by chemical products comprising the polymer structures according to the invention or a composite according to the invention. Preferred chemical products are, in particular, foams, shaped articles, fibers, foils, films, cables, sealing materials, liquid-absorbing hygiene articles, in particular nappies and sanitary towels, carriers for plant or fungal growth-regulating agents or plant protection active compounds, additives for building materials, packaging materials or soil additives.

The use of the polymer structures according to the invention or of the composite according to the invention in chemical products, preferably in the abovementioned chemical products, in particular in hygiene articles, such as nappies or sanitary towels, and the use of the superabsorber particles as carriers for plant or fungal growth-regulating agents or plant protection active compounds also make a contribution towards achieving the abovementioned objects. In the use as a carrier for plant or fungal growth-regulating agents or plant protection active compounds, it is preferable for the plant or fungal growth-regulating agents or plant protection active compounds to be able to be released over a period of time controlled by the carrier.

The invention will now be explained in more detail with the aid of figures, test methods and non-limiting examples.

Test Methods

Determination of the SFC Value and the TB Value

The SFC value and the TB value are determined in accordance with the test methods described in DE-A-102 49 821.

Determination of the Whiteness Index

The whiteness index is defined via the L*,a*,b* color system. The "L*" value represents the lightness (100-0), the "a*" value represents the red content (+) or the green content (−) and the "b*" value represents the yellow content (+) or the blue content (−). This scaling is based on the principles described in ASTM E 308 *"Standard Practice for Computing the Colors of Objects Using the CIE System"*.

The L*,a*,b* color values are determined by means of a "Hunter LabScanXE" spectrocolorimeter (Hunter Associates Laboratory, Reston, Va., USA) with the following settings:

| "Mode" | 0/45 |
|---|---|
| "Area View" | 44.5 mm |
| "Port Size" | 50.8 mm |
| "UV Filter" | nominal |

Before each measurement the LabScan XE is calibrated by first clamping the black glass plate belonging to the equipment accessories between the sample tray and measurement opening, the glass plate being laid on a Petri dish (diameter 100 mm, depth: 15 mm) and the calibration with the black glass plate being completed by operating the "OK" switch. The white standard plate is then laid on the Petri dish in the same manner and the calibration is completed again by operating the "OK" switch.

After the calibration has been performed, the "Read Std" switch is pressed in order to test the functional capacity of the measuring instrument, the standard plate not yet being removed here. For measurement of the L*,a*,b* color values for the standard plate, the "Read" switch is then operated.

The standard plate is then removed and the Petri dish is filled with the water-absorbing polymer structure to be measured, the product surface being smoothed with a doctor blade. By pressing the "Read Sam" switch, the sample is measured.

The whiteness index is defined as (L*/b*)=a*

EXAMPLES

Preparation of the Water-Absorbing Polymer Structure

A monomer solution consisting of 640 g of acrylic acid, which had been neutralized to the extent of 70 mol % with sodium hydroxide solution (497.36 g of 50% strength NaOH), 825.06 g of water, 2.102 g of polyethylene glycol 300 diacrylate (76.1%) and 4.010 g of polyethylene glycol monoallyl ether (79.8%, molecular weight about 440 g/mol) was freed from dissolved oxygen by flushing with nitrogen and cooled to the start temperature of 4° C. When the start temperature was reached, the initiator solution (0.8 g of sodium peroxydisulphate in 10 g of H$_2$O, 0.6 g of 35% strength hydrogen peroxide solution in 10 g of H$_2$O and 0.06 g of ascorbic acid in 10 g of H$_2$O) was added. When the end temperature of approx. 100° C. was reached, the gel formed was comminuted with a meat mincer and dried in a drying cabinet at 150° C. for 2 hours. The dried polymer was coarsely crushed, ground by means of a ring-beater mill (Retsch ZMI) with a 5 mm sieve and sieved to a powder having a particle size of from 150 to 850 μm.

Surface Modification

The polymer obtained above was mixed with an aqueous solution containing the components stated in the following Table 1 and the mixture was heated at 180° C. for 30 minutes (the wt. % data relate to the amount of polymer employed):

TABLE 1

| | Comparison example | Example 1 | Example 2 | Example 3 |
|---|---|---|---|---|
| Ethylene carbonate [wt. %] | 1.0 | 1.0 | 1.0 | 1.0 |
| Water [wt. %] | 3.0 | 3.0 | 3.0 | 3.0 |
| Aluminum lactate [wt. %] | 0.4 | 0.4 | 0.4 | 0.4 |
| Aluminum sulphate[1) [wt. %] | 0.3 | 0.3 | 0.3 | 0.3 |
| Sulphonate[2) [wt. %] | — | 0.15 | 0.2 | 0.25 |

[1)Employed as $Al_2(SO_4)_3 \times 14\, H_2O$
[2)The disodium salt of 2-hydroxy-sulphonatoacetic acid in pure form The permeability, the retention and also the whiteness index of the water-absorbing polymer structures obtained in this way were determined. The results are to be found in the following Table 2:

TABLE 2

| | Comparison example | Example 1 | Example 2 | Example 3 |
|---|---|---|---|---|
| SFC value [$\times 10^{-7}$ cm$^3 \cdot$ s/g] | 75 | 93 | 73 | 73 |
| TB value [g/g] | 29.3 | 29.7 | 29.9 | 30.4 |
| AAP value [g/g] | 25.1 | 25.4 | 25.5 | 25.5 |
| Whiteness index | 2.2 | 8.3 | 8.1 | 9.3 |

It can be seen from Table 2 that compared with conventional polymers the polymers according to the invention have a significantly improved whiteness index with comparable absorption properties. With the polymers obtained in Examples 1 to 3 no unpleasant odor at all was to be perceived, even after storage for 20 days at 60° C. and at 75% relative atmospheric humidity.

The invention claimed is:
1. A process for the production of water-absorbing polymer structures, comprising the process steps:
   i) providing an aqueous monomer solution containing
      a polymerizable, monoethylenically unsaturated monomer (α1) carrying acid groups or a salt thereof,
      optionally a monoethylenically unsaturated monomer (α2) which can be polymerized with the monomer (α1), and
      optionally a crosslinking agent (α3),
   ii) radical polymerizing the aqueous monomer solution to give a polymer gel,
   iii) optionally comminutating the polymer gel,
   iv) drying of the optionally comminuted polymer gel to give water-absorbing polymer structures,
   v) optionally grinding and sieving of the water-absorbing polymer structures and
   vi) surface post-crosslinking of the optionally ground and sieved water-absorbing polymer structures,
   wherein
   a reducing agent comprising a sulphonate, a salt of a sulphonate or a mixture of a sulphonate and a salt of a sulphonate is added to
   I) the aqueous monomer solution before or while carrying out process step ii),
   II) the polymer gel after carrying out process step ii),
   III) the optionally comminuted polymer gel after carrying out process step iii),
   IV) the water-absorbing polymer structure after carrying out process step iv),
   V) the water-absorbing polymer structure after carrying out process step v), or
   VI) the water-absorbing polymer structure after carrying out process step vi).

2. The process according to claim 1, wherein the reducing agent is added after carrying out process step iv) or after carrying out process step v) but before carrying out process step vi).

3. The process according to claim 1, wherein the reducing agent comprises less than 10 wt. % of sulphur compounds which differ from sulphonates, based on the total weight of the reducing agent.

4. The process according to claim 3, wherein the reducing agent comprises less than 10 wt. % of sulphites, bisulphites, sulphinates or salts of these sulphur compounds, based on the total weight of the reducing agent.

5. The process according to claim 1, wherein the sulphonate or the sulphonate salt has the structure I

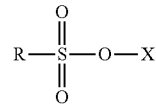

Structure 1 in which X is a hydrogen atom, an ammonium cation or an alkali metal cation and R is
   a saturated or unsaturated, aliphatic or aromatic $C_1$-$C_{20}$-hydrocarbon radical,
   a radical of the structure YOOC—$R^1$—, in which Y is a hydrogen atom, an ammonium cation or a monovalent metal cation and $R^1$ is a $C_1$-$C_7$-alkylene radical,
   a radical of the structure ZOOC—$R^2$—, in which Z is a hydrogen atom, an ammonium cation or a monovalent metal cation and $R^2$ is a $C_1$-$C_7$-alkylene radical, which carries a hydroxyl group on at least one of the carbon atoms,
   a radical of the structure R'R"N—$R^3$—, in which $R^3$ is a $C_1$-$C_9$-alkylene radical and the radicals R' and R" can be a hydrogen atom, a $C_1$-$C_5$-alkyl radical or a radical of the structure R'"—CO—, in which R'" is a saturated or unsaturated $C_1$-$C_5$-hydrocarbon, or
   a radical of the structure $R^4$—[OCH$_2$CH$_2$]$_n$—O—$R^5$- or a radical of the structure $R^4$—[OCH$_2$CHCH$_3$]$_n$—O—$R^5$—, in which $R^4$ is a $C_1$-$C_{10}$-alkyl radical or a $C_1$-$C_9$-acyl radical, n is an integer in a range of from 2 to 50 and $R^5$ is a $C_1$-$C_9$-alkylene radical.

6. The process according to claim 1, wherein the sulphonate or the sulphonate salt is chosen from the group consisting of vinylsulphonic acid, allylsulphonic acid, vinyltoluenesulphonic acid, styrenesulphonic acid, sulphoethyl acrylate, sulphoethyl methacrylates, sulphopropyl acrylates, sulphopropyl methacrylates, 2-vinyl-4-ethylbenzenesulphonic acid, 2-allylbenzenesulphonic acid, 1-phenylethylenesulphonic acid, 2-hydroxy-3-methacryloxypropylsulphonic acid, 2-acrylamide-2-methylpropanesulphonic acid, para-toluenesulphonic acid, 2-hydroxy-2-sulphonatoacetic acid, salts of the abovementioned compounds or a mixture of at least two of these.

7. The process according to claim 1, wherein the sulphonate salt comprises disodium salt of 2-hydroxy-2-sulphonatoacetic acid.

8. The process according to claim 1, wherein the reducing agent is employed in an amount in a range of from about 0.001 to about 10 wt. %, based on the solids content of the water-absorbing polymer structure.

9. The process according to claim 1, wherein the reducing agent is added in the form of a fluid comprising the reducing agent and a solvent.

10. The process according to claim 9, wherein the solvent is water.

11. A water-absorbing polymer structure obtainable by a process according to claim 1.

12. A water-absorbing polymer structure comprising about 10 to about 100,000 ppm, based on the solids content of the water-absorbing polymer structure, of a non-polymerized sulphonate, a non-polymerized salt of a sulphonate or a mixture of a non-polymerized sulphonate and a non-polymerized salt of a sulphonate, and less than 1,000 ppm, based on the solids content of the water-absorbing polymer structure, of non-polymerized sulphites, non-polymerized bisulfites, non-polymerized sulphinates or non-polymerized salts of these compounds.

13. A water-absorbing polymer structure, the surface of which has been brought into contact with about 0.001 to about 10 wt. %, based on the solids content of the water-absorbing polymer structure, of a reducing agent comprising a sulphonate, a salt of a sulphonate or a mixture of a sulphonate and a salt of a sulphonate.

14. The water-absorbing polymer structure according to claim 13, wherein the reducing agent comprises less than 10 wt. %, based on the total weight of the reducing agent, of sulphur compounds which differ from sulphonates.

15. The water-absorbing polymer structure according to claim 13, wherein the reducing agent comprises less than 10 wt. %, based on the total weight of the reducing agent, of sulphites, bisulphites, sulphinates or salts of these sulphur compounds.

16. The water-absorbing polymer structure according to claim 12, wherein the sulphonate or the salt of a sulphonate is a sulphonate or a salt of a sulphonate has the structure I

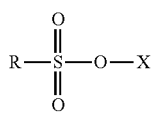

Structure 1 in which X is a hydrogen atom, an ammonium cation or an alkali metal cation and R is
   a saturated or unsaturated, aliphatic or aromatic $C_1$-$C_{20}$-hydrocarbon radical,
   a radical of the structure YOOC—$R^1$—, in which Y is a hydrogen atom, an ammonium cation or a monovalent metal cation and $R^1$ is a $C_1$-$C_7$-alkylene radical,
   a radical of the structure ZOOC—$R^2$—, in which Z is a hydrogen atom, an ammonium cation or a monovalent metal cation and $R^2$ is a $C_1$-$C_7$-alkylene radical, which carries a hydroxyl group on at least one of the carbon atoms,
   a radical of the structure R'R''N-$R^3$—, in which $R^3$ is a $C_1$-$C_9$-alkylene radical and the radicals R' and R'' can be a hydrogen atom, a $C_1$-$C_5$—alkyl radical or a radical of the structure R'''—CO—, in which R''' is a saturated or unsaturated $C_1$-$C_5$-hydrocarbon, or
   a radical of the structure $R^4$—[$OCH_2CH_2$]$_n$—O—$R^5$- or a radical of the structure $R^4$—[$OCH_2CHCH_3$]$_n$—O—$R^5$—, in which $R^4$ is a $C_1$-$C_{10}$-alkyl radical or a $C_1$-$C_9$-acyl radical, n is an integer in a range of from 2 to 50 and $R^5$ is a $C_1$-$C_9$-alkylene radical.

17. The water-absorbing polymer structure according to claim 11 having at least one of the following properties:
   (($\beta$1) a whiteness index, determined in accordance with the test method described herein, of at least about 7.5 after storage of the water-absorbing polymer structure for 20 days at 60° C. and at 75% relative atmospheric humidity;
   (($\beta$2) an absorption, determined in accordance with ERT 442.2-02, under a pressure of about 50 g/cm² (0.7 psi) of at least about 18 g/g;
   (($\beta$3) an SFC value (SFC="saline flow conductivity"), determined in accordance with the test method described herein, at a TB value of <26 g/g, determined in accordance with the test method described herein, of at least about $80\times10^{-7}$ cm³·s·g⁻¹,
   ($\beta$4) an SFC value, determined in accordance with the test method described herein, at a TB value in the range of >26 to <27 g/g, determined in accordance with the test method described herein, of at least about $70\times10^{-7}$ cm³·s·g⁻¹,
   ($\beta$5) an SFC value, determined in accordance with the test method described herein, at a TB value in the range of >27 to <28 g/g, determined in accordance with the test method described herein, of at least about $60\times10^{-7}$ cm³·s·g⁻¹,
   ($\beta$6) an SFC value, determined in accordance with the test method described herein, at a TB value in the range of >28 to <29 g/g, determined in accordance with the test method described herein, of at least about $45 \times10^7$ cm³·s·g⁻¹,
   ($\beta$7) an SFC value, determined in accordance with the test method described herein, at a TB value in the range of >29 to <30 g/g, determined in accordance with the test method described herein, of at least about $30\times10^{-7}$ cm³·s·g⁻¹,
   ($\beta$8) an SFC value, determined in accordance with the test method described herein, at a TB value in the range of >30 to <31 g/g, determined in accordance with the test method described herein, of at least about $20\times10^{-7}$ cm³·s·g⁻¹,
   ($\beta$9) an SFC value, determined in accordance with the test method described herein, at a TB value in the range of >31 g/g, determined in accordance with the test method described herein, of at least about $10\times10^{-7}$ cm³·s·g⁻¹.

18. The water-absorbing polymer structure according to claim 11, comprising about 10 to about 100,000 ppm, based on the solids content of the water-absorbing polymer structure, of a non-polymerized sulphonate, a non-polymerized salt of a sulphonate or a mixture of a non-polymerized sulphonate and a non-polymerized salt of a sulphonate, and less than about 1,000 ppm, based on the solids content of the water-absorbing polymer structure, of non-polymerized sulphites, non-polymerized bisulfites, non-polymerized sulphinates or non-polymerized salts of these compounds.

19. A composite comprising a water-absorbing polymer structure according to claim 11 and a substrate.

20. A process for the production of a composite, wherein a water-absorbing polymer structure according to claim 11 and a substrate and optionally an auxiliary substance are brought into contact with one another.

21. A composite obtainable by a process according to claim 20.

22. An article selected from foams, shaped articles, fibers, foils, films, cables, sealing materials, liquid-absorbing hygiene articles, carriers for plant and fungal growth-regulating agents, packaging materials, soil additives or building materials comprising the water-absorbing polymer structure according to claim 11.

23. A use of the water-absorbing polymer structure according to claim 11, the use comprising providing the water-absorbing polymer structure in foams, shaped articles, fibers, foils, films, cables, sealing materials, liquid-absorbing hygiene articles, carriers for plant and fungal growth-regulating agents, packaging materials, soil additives, for controlled release of active compounds, or in building materials.

24. The process according to claim 1, wherein the sulphonate salt comprises 2-hydroxy-2-sulfonatoacetic acid.

25. The water-absorbing polymer structure according to claim 12, wherein the sulphonate salt comprises 2-hydroxy-2-sulfonatoacetic acid.

26. The water-absorbing polymer structure according to claim 13, wherein the sulphonate salt comprises 2-hydroxy-2-sulfonatoacetic acid.

* * * * *

UNITED STATES PATENT AND TRADEMARK OFFICE
CERTIFICATE OF CORRECTION

PATENT NO. : 8,372,920 B2
APPLICATION NO. : 12/740054
DATED : February 12, 2013
INVENTOR(S) : Mirko Walden It is certified that error appears in the above-identified patent and that said Letters Patent is hereby corrected as shown below:

<u>Column 3</u>,

Lines 49-51, remove hard line break between "accordance with" and "ERT 420.2-02".

<u>Column 20, Claim 17</u>,

Line 23, ">26 to <27 g/g" should read --$\geq$26 to <27 g/g--.

Line 28, ">27 to <28 g/g" should read --$\geq$27 to <28 g/g--.

Line 29, remove bold font from "$60 \times 10^{-7}$".

Line 33, ">28 to <29 g/g" should read --$\geq$28 to <29 g/g--.

Line 34, remove bold font from "$45 \times 10^{-7}$".

Line 38, ">29 to <30 g/g" should read --$\geq$29 to <30 g/g--.

Line 39, remove bold font from "$30 \times 10^{-7}$".

Line 43, ">30 to <31 g/g" should read --$\geq$30 to <31 g/g--.

Line 48, ">31 g/g" should read --$\geq$31 g/g--.

Line 49, remove bold font from "$10 \times 10^{-7}$".

Signed and Sealed this
Ninth Day of April, 2013

Teresa Stanek Rea
*Acting Director of the United States Patent and Trademark Office*